United States Patent [19]

Takemoto et al.

[11] 4,162,576
[45] Jul. 31, 1979

[54] APPLIANCES FOR TREATING TEETH

[75] Inventors: Kiyochika Takemoto, Kodaira; Yasuo Suzuki, Higashi Kurume; Yoshihito Ochiai, Fujisawa; Syozi Nakashima, Ninomiya; Midori Hayashi, Yamakita, all of Japan

[73] Assignee: Lion Hamigaki Kabushiki Kaisha, Japan

[21] Appl. No.: 780,367

[22] Filed: Mar. 23, 1977

[30] Foreign Application Priority Data

Mar. 24, 1976 [JP] Japan .................... 51-35364[U]

[51] Int. Cl.² .................................................. A61C 3/00
[52] U.S. Cl. .............................. 32/40 R; 128/62 A;
128/66; 128/229
[58] Field of Search .............. 15/22 R, 24 A; 128/32,
128/38, 66, 65, 62 A, 260; 32/40, 58, DIG. 4

[56] References Cited
U.S. PATENT DOCUMENTS 3,840,992 10/1974 English .......................... 128/62 A Primary Examiner—Robert Peshock
Attorney, Agent, or Firm—Steinberg & Blake

[57] ABSTRACT

An appliance for treating teeth, such as human teeth, by providing them with a reinforcing acid-resistant layer of a tooth decay retarding agent. The appliance includes a vibrator for producing ultrasonic vibrations, this vibrator terminating in an elongated vibratory tip. A casing houses the vibrator and has a tubular open end region in which the tip is at least partly accommodated. This tubular open end region of the casing carries an elastic membrane wall which extends across the tubular open end region of the casing and through which the tip extends so that the tip has a free end situated outwardly beyond this elastic membrane wall. The elastic membrane wall fluid-tightly engages the vibratory tip while surrounding the latter, and the membrane wall maintains this fluid-tight engagement with the tip during vibration thereof. The tubular open end of the casing is adapted to be attached to a tray which has a hollow interior provided with a liquid vibration-transmitting medium, the tip piercing into the interior of the tray to engage the liquid medium therein when the tray is attached to the casing at the tubular open end region thereof.

3 Claims, 12 Drawing Figures

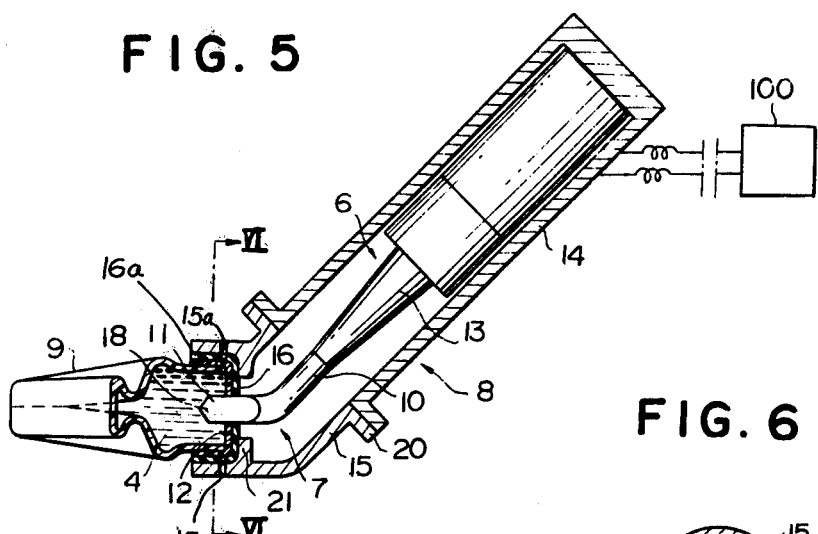
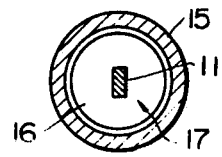
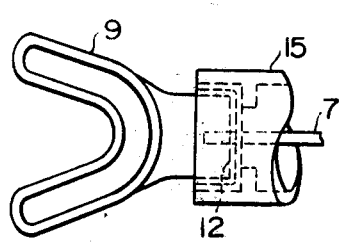
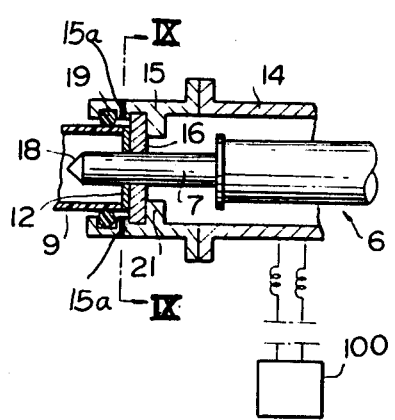
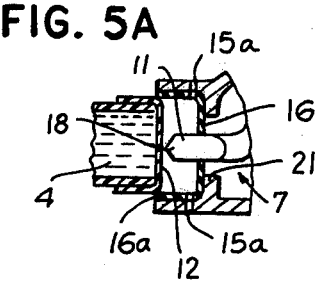

FIG. 9
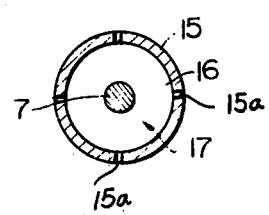
FIG. 10B
FIG. 10A
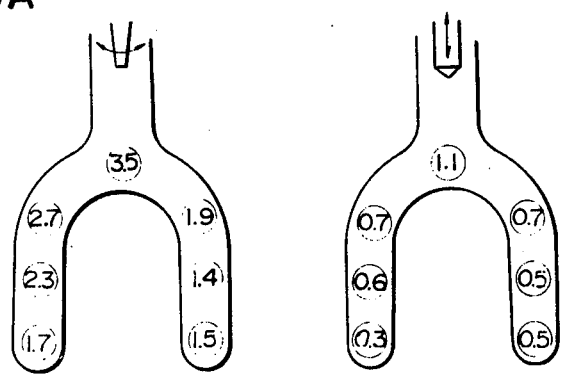

4,162,576

APPLIANCES FOR TREATING TEETH

BACKGROUND OF THE INVENTION

The present invention relates to appliances for treating teeth, particularly human teeth.

In particular, the present invention relates to an apparatus to be utilized for applying to teeth a reinforcing acid-resistant layer of a tooth decay retarding agent. The invention relates especially to an apparatus which is capable of exposing teeth to the radiation of ultrasonic waves while the teeth are engaged by the decay retarding agent.

In order to prevent or retard tooth decay, it has already been proposed to apply manually to the teeth which are to be treated a solution of a tooth decay retarding agent such as tin fluoride, sodium fluoride, or fluoramine. However, if only the decay retarding agent is coated on the surface of the teeth, the coating adheres poorly to the teeth and is readily dissolved away and removed from the tooth surface in a relatively short time. Thus, through measures of this type it is impossible to achieve a long-lasting decay-retarding effect. Moreover, if a coating of a tooth decay retarding agent is situated only at the surface of the teeth, it is not possible to achieve also an effective prevention of dissolving of calcium from the tooth surface.

It has been discovered, however, that the above drawbacks can be eliminated if the teeth are exposed to the radiation of ultrasonic waves while the teeth are engaged by the tooth-decay retarding agent. However, an apparatus for effectively carrying out such a treatment has been difficult to develop. Thus, a tray for receiving the teeth while the latter are engaged by the decay retarding agent has been developed, this tray having a hollow interior containing a liquid medium for transmitting the ultrasonic vibrations. However, when a vibrating means is attached to such a tray, unavoidable difficulties are encountered in connection with preventing the liquid medium from receiving air or air bubbles or from spilling undesirably, so that the desired results are difficult to achieve with such an apparatus.

SUMMARY OF THE INVENTION

It is accordingly a primary object of the present invention to provide an apparatus which will avoid the above drawbacks.

In particular, it is an object of the present invention to provide an apparatus according to which it becomes possible to connect to a tray of the above type a vibrating means in such a way that there will be no loss of the liquid vibration-transmitting medium and at the same time there will be a reliable prevention of incorporation of air bubbles or other substances into the interior tray space where the liquid vibration-transmitting medium is situated.

Also, it is an object of the present invention to provide a structure of the above type which will afford an easy connection and disconnection of a tray of the above type to a vibrating means.

According to the invention the apparatus includes a vibrator means which has a vibratory tip which is vibrated at an ultrasonic frequency by the vibrator means. A casing means carries the vibrator means and has a tubular open end region in which the vibratory tip is at least partially accommodated. An elastic membrane wall is carried by the casing means extending across the open tubular end region thereof, and the vibratory tip of the vibrator means extends through this membrane wall. The membrane wall has a fluid-tight engagement with the vibratory tip, and this fluid-tight engagement is maintained while the vibratory tip is vibrated. A free end portion of the vibratory tip extends outwardly beyond the membrane wall to be received in the interior of a tray means where a liquid vibration-transmitting medium is situated, with the construction being such that when the tray means is attached to the tubular open end region of the casing means the vibratory tip will penetrate into the interior of the tray means while at the same time there will be a prevention of loss of the vibration-transmitting liquid and also a prevention of the incorporation of air bubbles into the interior of the tray means where the liquid vibration-transmitting medium is situated.

BRIEF DESCRIPTION OF DRAWINGS

The invention is illustrated by way of example in the accompanying drawings which form part of this application and in which:

FIG. 5 is a longitudinal sectional elevation of an embodiment of an appliance according to the invention;

FIG. 5A shows part of the structure of FIG. 5 during assembly of a tray means with a casing means which carries a vibrator means;

FIG. 6 is a transverse section of the structure of FIG. 5 taken along line VI—VI of FIG. 5 in the direction of the arrows with the tray means being omitted from FIG. 6;

FIG. 7 is a fragmentary top plan view of the structure of FIG. 5 showing the tray means and the part of the casing means assembled therewith;

FIG. 8 is a fragmentary longitudinal sectional elevation of another embodiment of a structure of the invention;

FIG. 9 is a transverse section of the structure of FIG. 8 taken along line IX—IX of FIG. 8 in the direction of the arrows with the tray means also being omitted from FIG. 9; and FIGS. 10A and 10B respectively illustrate schematically results achieved with the embodiments of FIGS. 5 and 8, respectively.

DESCRIPTION OF PREFERRED EMBODIMENTS

As has been indicated above, it has been found that surprisingly effective results can be achieved if the teeth are exposed to the effects of the radiation of ultrasonic waves while the teeth are engaged by a decay-retarding agent. The result of this treatment is to form a reinforcing layer of the decay-retarding agent which covers and penetrates into the teeth. Moreover, the effects include excellent results with respect to prevention of dissolving out of calcium as well as reinforcing the tooth surface. These results are apparent from FIGS. 1 and 2.

Figure 1:
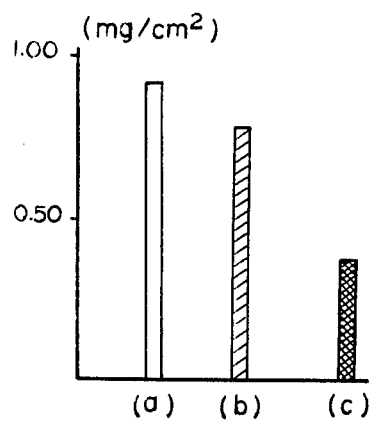
FIGS. 1 and 2 are graphs illustrating the results achieved with the treatment of the invention.

Referring to FIG. 1, the graph illustrated therein indicates at the ordinate the amounts of calcium ions ($Ca^{2+}$) dissolved out of the teeth after dipping thereof for 5 hours in an acetic acid buffer solution having a concentration of 0.1 mole per liter at 37° C. The bar (a) of FIG. 1 shows the results of tests made on an untreated human tooth sample. The bar (b) shows the results of a test made on a human tooth sample which was only dipped in an aqueous solution containing 8% of $SnF_2$ for 5 minutes, with of course the tooth which was treated in this way also being dipped for 5 hours in the above acetic acid buffer solution under the above conditions utilized for the untreated tooth sample. The bar c shows the results of a test made on a human tooth sample which was exposed to radiation of ultrasonic waves at a frequency of 19 KHz for 3 minutes while the tooth sample was engaged by an aqueous solution containing 8% of $SnF_2$. Of course, this latter sample also was dipped in the acetic acid buffer solution for 5 hours as described above in connection with the untreated sample. It is thus apparent that with the sample treated in the presence of the ultrasonic waves as described above, the prevention of dissolving out of calcium ions is greatly improved as compared to the samples (a) and (b).

Figure 2:
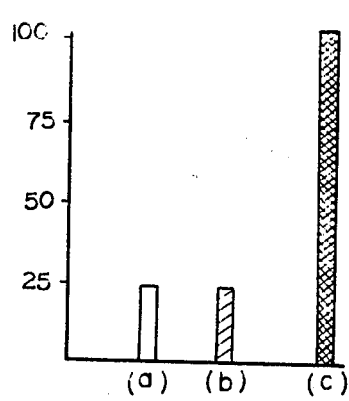

The graph of FIG. 2 shows at the ordinate Vickers hardness of the three samples used for the graph of FIG. 1, all of the samples having been dipped in an acetic acid buffer solution having a concentration of 0.1 mole per liter for 5 hours at 37° C. in order to bring about deliming. Thus, it is clear from FIG. 2 that as between the untreated sample and the sample which was only dipped in the aqueous solution of 8% $SnF_2$, there is almost no difference, whereas with the sample (c) a tremendous improvement is achieved.

Figure 3:
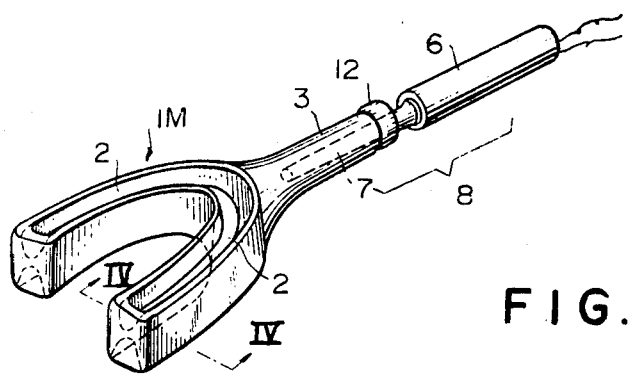
FIG. 3 is a perspective illustration of an example of an appliance for treating the teeth.

While it is of course evident that a treatment as shown at the bars (c) of FIGS. 1 and 2 is highly desirable, an appliance for carrying out this treatment has up to the present time not been provided in a fully satisfactory manner. For example, as shown in FIG. 3, it is possible to utilize a vessel-like tray for treating all of the teeth of the upper and lower rows simultaneously according to the above-mentioned treatment. This tray of FIG. 3 has a substantially Y-shaped configuration including a portion 1M which is of a horseshoe-shaped configuration so that this configuration will match that of the rows of teeth. The tray is formed with upper and lower U-shaped grooves 2 for respectively receiving the upper and lower rows of teeth. Thus, this portion 1M of the tray means of FIG. 3 is substantially H-shaped in cross section, as is also apparent from FIG. 4. The horseshoe-shaped portion 1M forms an extension of an integral tubular handle portion 3, and this tubular handle portion 3 is hollow and has its hollow interior communicating with the interior of the portion 1M. Thus, the communicating hollow interiors of the portion 1M and handle portion 3 of the tray means are filled with a liquid ultrasonic wave-transmitting medium 4 (FIG. 4) such as degasified water or silicon oil. The wall 5 of the tray means is made of a relatively soft flexible thin film of a material which is capable of transmitting the ultrasonic waves therethrough while preventing the ultrasonic wave transmitting medium from passing through this wall. Thus the wall 5 of the tray means may be made of aluminum foil, a suitable plastic material, or rubber. This tray means is introduced into the oral cavity and the teeth of the upper and lower rows are situated in the grooves 2 while the wall 5 of the tray means is caused to adhere closely to the surface of the teeth as is apparent from FIG. 4 in particular, these walls 5 also engaging part of the gingiva.

A horn-like vibratory tip 7 is attached to an end of a known ultrasonic vibratory means 6 forming part thereof, with this tip 7 situated in the interior of the hollow handle portion 3 of the tray means. Thus the vibratory means 6 and the vibratory tip 7 together form a vibrator means 8.

A liquid or pasty tooth-decay retarding agent having ingredients as referred to above, such as tin fluoride, is coated on the surface of the teeth or situated at the interior of the grooves 2, and the tray is situated in the oral cavity with the upper and lower rows of teeth situated in the grooves 2 and with the tray means being clamped between the teeth which bite the tray means. In this way, particularly because the wall 5 is flexible, the surfaces which define the grooves 2 adhere closely to the surface of the teeth while the layer of tooth-decay retarding agent also is situated in engagement with the teeth. With the appliance in this latter condition, the vibratory means 6 of the vibrator means 8 is set into operation at an appropriate frequency preferably selected within a range of from 10 KHz to 500 KHz, so that the ultrasonic waves will be radiated from the vibratory tip 7 and transmitted through the transmitting medium 4 to the horseshoe-shaped portion 1M of the tray means. Thus, the ultrasonic vibrations pass through the wall 5 as well as the tooth-decay retarding agent and reach the surface of the teeth. As a result the surface portions of the teeth are impregnated with the tooth decay retarding agent and a durable reinforcing layer is provided, this layer having a great tooth decay retarding effect.

Figure 4:
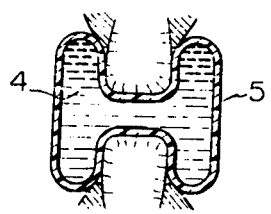
FIG. 4 is a section taken along line IV—IV of FIG. 3 in the direction of the arrows and schematically illustrating how teeth are treated.

In utilizing an appliance as shown in FIGS. 3 and 4, the vibrator means 8 is attached to the tray means which preferably is discarded after a treatment, so that a sanitary treatment is assured. The tray means is relatively inexpensive and can be discarded after being used. However, the vibrator means 8 is relatively expensive while at the same time has a long operating life and is extremely robust and reliable in operation so that it may be used repeatedly. Thus, after each treatment it is necessary to attach a new tray to the vibrator means. The ultrasonic wave transmitting medium such as degasified water or the like is situated in the interior of the tray means. If different substances or air bubbles become included in this liquid wave-transmitting medium particularly during the treatment, a good transmission of ultrasonic waves is prevented and there is a risk that the intended ultrasonic treatment effect will not be sufficiently achieved. Thus, before the treatment degasified water is filled into the interior of the tray means and sealed by the walls thereof such as the wall 5 made of a laminated film or aluminum foil. However, when the treatment is started, part of the wall 5 must be removed or broken through so as to enable the vibratory tip 7 of the vibrator means 8 to be received in the hollow interior of the tray means. In the event that the introduction of the vibratory tip 7 into the hollow interior of the tray means is not properly carried out with a great deal of care, some of the degasified water is lost or different substances or air bubbles are often incorporated into the liquid medium 4. It is extremely difficult to prevent this disadvantage from occurring, so that this disadvantage is a drawback of an apparatus as shown in FIGS. 3 and 4.

Referring now to FIGS. 5–7, the embodiment of the invention which is illustrated therein includes a vibrator means 8 of the type described above in connection with FIG. 3. In this embodiment the vibratory means 6 of the vibrator means 8 is a torsional vibrator for providing ultrasonic vibrations, and the vibrator means 8 includes in this embodiment an angled vibratory tip 7 which oscillates angularly. Thus the vibratory tip 7 includes an elongated shaft portion 10 which terminates in an elongated relatively thin flat portion 11. This vibratory tip 7 is connected at its shaft portion 10 which is distant from the wing or flat portion 11 to the vibratory means 6. The vibrator means 8 is carried by a casing means 15 having at its lower end, as viewed in FIG. 5, an open tubular end region which accommodates the tip 7 and in particular the flat wing portion 11 thereof. This casing means 15 together with the vibrator means 8 are adapted to be connected to the illustrated tray means 9. This tray means 9 has substantially the same construction as the tray means of FIGS. 3 and 4 and is filled in its interior with the liquid wave-transmitting medium 4 capable of transmitting the ultrasonic waves. Before the tray means 9 is attached to the casing means 15, the free end of the tubular handle portion of the tray means 9 is sealed by an end wall of the tray means in the form of a suitable film 12 having the form of a laminated film or aluminum foil. However, when the tray means 9 is attached to the casing means 15, the vibratory tip 7 will pierce at its portion 11 through the wall 12, breaking through the latter to form an opening therein. The vibratory means 6 when energized by the source of ultrasonic vibrations 100, schematically illustrated in FIG. 5, will cause angular oscillation of the tapered shaft portion 13 of the vibratory means 6, this tapered shaft portion 13 being fixed in any suitable way to the portion 10 of the tip 7. Such angular vibration can be produced in a well known manner. The vibratory means 6 is contained in the casing portion 14 of the casing means 15, this casing portion 14 being attached to the flange 20 of the casing means 15.

In accordance with the invention the tubular open end region of the casing means 15 has in its interior a transverse elastic membrane wall 16. Thus, adjacent its open outer end the casing means 15 has in its interior an annular flange 21 against which the membrane wall 16 is situated as by being adhered thereto, for example. Thus the flange 21 will support the membrane wall 16. This membrane wall 16 is composed of a material which has a suitable strength while at the same time having a suitable elasticity, such as natural rubber, silicon rubber, synthetic rubber or the like. The portion 11 of the vibratory tip 7 extends through the membrane wall 16 while the latter fluid-tightly engages the tip 7 at its relatively flat portion 11 which is of the rectangular cross section shown in FIG. 6. The portion 11 of the tip 7 can simply be pierced through the membrane wall 16 which due to its elasticity will tightly grip the portion 11 in a fluid-tight manner, with this fluid-tight engagement being maintained during vibration of the tip 7. The oscillatory angular vibration of the tip 7 which is angled as illustrated is preferred inasmuch as with this construction a considerable amplitude can be provided for the relatively flat portion 11 with a relatively small amount of energy consumed by the vibrator means 8. Thus, the membrane wall 6 will have a suitable pliability or flexibility while at the same time a considerable toughness.

Thus, since the membrane wall 16 is made of an elastic material as mentioned above, even though the flat portion 11 of the tip 7 pierces through the membrane wall 16, nevertheless the latter closesly adheres to the portion 11 due to the elasticity of the wall 16, so that a seal is maintained between the opposed faces of the wall 16.

The surface 17 of the wall 16, which is directed toward the open end of the casing means 15, as indicated in FIG. 6, constitutes a pressing surface which closely presses against the end wall 12 of the tray means 9. The tubular open end region of the casing means 15 which receives the tubular end portion of the tray means 9 is of a circular cylindrical configuration, as is apparent particularly from FIG. 6, and the wall 16 has a cylindrical extension 16a extending along the inner surface of the casing means 15 from the wall 16 to the free end of the casing means 15 to form a seal. In addition, the cylindrical portion 15 is formed with a plurality of small openings 15a passing through the wall of the tubular portion of casing means 15 and through the extension 16a of membrane wall 16 adjacent to the wall 16 in the manner apparent from FIGS. 5 and 6. These openings 15a are small enough to permit air to pass therethrough but too small to permit any liquid to pass therethrough.

Thus, when the tubular free end portion of the tray means 9 is introduced into the open end region of the casing means 15, as indicated in FIG. 5A, the extension 16a of the membrane wall 16 will have a slidable fluid-tight engagement with the part of the end wall 12 which circumferentially surrounds the free end region of the tray means 9 which is received in the space surrounded by the extension 16a. It will be noted from FIG. 5A that this sealing slidable engagement between the tray means and the casing means 15 is provided before the portion 11 of tip 7 pierces through the wall 12, this portion 11 terminating in a relatively sharp pointed tip 18 to facilitate piercing through the wall 12. Thus it will be seen that this pointed part 18 is situated between the plane which contains the outer end face of the casing means 15 and the plane in which the membrane wall 16 is located. It is of course not essential that the seal be provided by way of an extension 16a of the membrane wall 16. Instead a suitable sealing ring may be provided for this purpose if desired. As is apparent from FIG. 5A as the tubular end portion of the tray means 9 is introduced into the cavity defined by the extension 16a, air trapped between the end wall 12 and the membrane wall 16 can flow out through the openings 15a so that such air will not be incorporated into the liquid wave-transmitting medium 4, while at the same time if any liquid should spill it will not be capable of flowing through the relatively small openings 15a. However, liquid generally will not spill out of the interior of the tray means 9 because as the portion 11 of the tip 7 pierces through the wall 12 it displaces liquid away from the opening formed in the wall 12.

Thus, as the tray means continues to be introduced into the tubular open end region of the casing means 15, in the manner shown in FIG. 5A, the tray means will assume with respect to the casing means 15 the position shown in FIG. 5, and now the structure is ready for use as described above in connection with FIGS. 3 and 4. The tray means will be reliably maintained connected to the remaining structure simply by friction. When the structure has the condition shown in FIG. 5 the wall 12 presses against the surface 17 of the membrane wall 16. Thus the end region of the tray means 9 which is received in the tubular portion of the casing means 15 is fully sealed and the vibrations can be effectively transmitted with the membrane wall 16 yielding while maintaining a fluid-tight engagement all around the portion 11 of the tip 7. The edge of the opening formed in the wall 12 also adheres to the portion 11 of the tip 7. Thus, the ultrasonic wave transmitting medium 4 in the hollow interior of the tray means 9 is prevented from leaking and also incorporation of foreign substances or air bubbles into the interior of the tray means from the outside is reliably avoided. In order to increase the frictional engagement between the tray means and casing means 15, the cylindrical portions thereof may be suitably tapered or a screw-thread type of connection may be provided.

With the above structure when the vibratory means 6 is energized at a frequency of from 10 to 500 KHz, the tip 7 will oscillate in a torsional manner and the portion 11 of the tip 7 will reproduce fine oscillatory vibrations about the axis of the shaft 13. The ultrasonic waves will radiate from the tip 7 through the medium 4 and arrive at the teeth which are received in the tray means 9 in the manner described above in connection with FIG. 3, so that a treatment as described above can be carried out.

Although the portion 11 of the tip 7 carries out the oscillatory vibrations referred to above, inasmuch as the amplitude of the vibration of the portion 11 is relatively small, on the order of about 10 to about 40 microns, even if the membrane wall 16 closely adheres to the tip 7 as a result of the elasticity of the wall 16 so as to prevent leakage of the medium 4, nevertheless vibrations are not inhibited by the membrane wall 16. Therefore leakage of the wave-transmitting medium to the exterior is reliably avoided while the leakage is also prevented to the mechanical vibrating structure, and at the same time incorporation of foreign bodies or air bubbles can be reliably avoided. The open end of the tray means 9 can readily be sealed by using a plastic cap instead of the end wall 12.

In the embodiment of the invention which is illustrated in FIGS. 8 and 9, use is made of a known longitudinal vibratory structure. Thus in this embodiment the vibratory means 6 of the vibrator means 8 is connected with an elongated tip 7 which is straight and which vibrates longitudinally along its central axis, this tip 7 also terminating in a sharply pointed tip 18. In this embodiment the casing means 15 has in its interior an elastic membrane wall 16 supported also by the interior annular flange 21 which is adhered to the membrane wall 16, for example. In this embodiment outwardly beyond the wall 16 the interior of the tubular open end region of the casing means 15 is formed with an annular groove which recieves the illustrated sealing ring 19, and as was the case with the embodiment of FIGS. 5-7, the front point 18 of the tip 7 will pierce through the wall 12 which closes off the end of the tubular portion of the tray means 9. This tip 7 of course pierces through the membrane wall 16 which fluid-tightly grips the tip 7 all around the axis thereof while at the same time the tip 7 can vibrate longitudinally. The structure of FIG. 8 and FIG. 9 operates in the same way as the structure of FIGS. 5-7 except that in this case the vibrations result from longitudinal reciprocation of the tip 7 along its central axis. FIG. 9 shows the surface 17 of the membrane wall 16 which presses against the wall 12 with openings 15a also being illustrated. Although the tip 7 vibrates longitudinally, inasmuch as the amplitude is very small, even if the membrane wall 16 closely adheres to the tip 7 as a result of elasticity of wall 16 nevertheless vibrations of the tip 7 are not inhibited in any way and leakage of the medium 4 is reliably prevented.

By providing the vibratory tip 7 with the sharp portion 18 so that the tip 7 has at its portion 18 a conical configuration, the peak of the characteristic of the sonic pressure is moderated and a good sonic pressure distribution is achieved.

In FIG. 8 as well as FIG. 7 an oscillator 100 is schematically illustrated operatively connected with the vibratory means 6.

Experiments which have been carried out have confirmed that exceedingly good results are obtained with the above structure of the invention utilizing either the torsional vibratory means of FIG. 5 or the longitudinal vibratory means of FIG. 8, these results being particularly effective with respect to transmission of ultrasonic waves in the tray means 9. Moreover, it has been confirmed that with respect to the sonic pressure distribution, the torsional vibrator means will produce superior results to the longitudinal vibrator means because the sonic pressure distribution in the tray means 9 is much more uniform when the torsional vibrator means of FIG. 5 is utilized. Results of experiments carried out are shown in FIGS. 10A and 10B.

Referring to FIG. 10A, there are illustrated therein results obtained when using a spatula-like torsional vibratory tip as shown in FIGS. 5 and 6. FIG. 10B shows the results obtained when using a longitudinal vibratory tip as shown in FIG. 8. In each of the experiments with these different tips, the distance between the free end of the vibratory tip and the position occupied by a front tooth is 4 cm while the vibration amplitude at the pointed portion 18 of the vibratory tip is on the order of 10 microns. In FIGS. 10A and 10B, the circled numerical values indicate the sonic pressure at the regions of the tray means where these sonic pressure values are located. Thus it is apparent that with the arrangement shown in FIG. 10A, utilizing the torsional vibrator of FIG. 5, greater and more uniform sonic pressures are achieved than in the case of FIG. 10B utilizing the longitudinal vibrator of FIG. 8.

With the above structure of the invention the tray means can easily be attached to and detached from the casing means 15. At the same time leakage of the transmitting medium is reliably avoided during the attachment and during the treatment. Also incorporation of different substances or air bubbles into the interior of the tray means from the exterior thereof is reliably avoided. Thus the appliance of the invention is highly practical and forms a valuable means to provide at the surface of teeth a reinforcing acid-resistant layer of a tooth decay retarding agent.

What is claimed is:

1. For use in applying to teeth a reinforcing acid-resistant layer of a tooth decay retarding agent, vibrator means for providing ultrasonic vibrations and including a vibratory tip, casing means housing said vibrator means and having a tubular open end region in the interior of which said vibratory tip is at least partly situated, and an elastic membrane wall carried by said casing means at said tubular open end region thereof and extending across said tubular open end region of said casing means, said vibratory tip extending through said elastic membrane wall while being surrounded and fluid-tightly engaged by said membrane wall, said membrane wall maintaining its fluid-tight engagement with said tip during vibration of the latter and further including a hollow tray means for receiving teeth which are to be treated, said hollow tray means having a hollow interior containing a liquid medium for transmitting the ultrasonic vibrations, and said tray means terminating in an elongated tubular portion adapted to be received in said tubular open end region of said casing means, said tubular portion of said tray means terminating in an end wall which when said tubular portion of said tray means is situated in said tubular open end region of said casing means becomes situated next to said membrane wall while said vibratory tip pierces through said end wall of said tray means to extend into and engage the liquid medium for transmitting vibrations through the latter to said tray means.

2. The combination of claim 1 and wherein said tubular open end region of said casing means is formed adjacent said membrane wall but outwardly of the latter with at least one opening passing through said casing means and while being too small to permit liquid to flow therethrough nevertheless permits air trapped between said end wall of said tray means and said membrane wall to escape from the space which exists temporarily between said end wall of said tray means and said membrane wall while said end wall of said tray means approaches said membrane wall.

3. The combination of claim 2 and wherein said casing means includes at said tubular open end region thereof a sealing means which fluid-tightly surrounds said tubular end portion of said tray means when the latter is situated in said tubular open end region of said casing means.

* * * * *